United States Patent
Fetzer et al.

[11] Patent Number: 6,072,087
[45] Date of Patent: *Jun. 6, 2000

[54] METHOD FOR PRODUCING CARBONYL COMPOUNDS

[75] Inventors: Thomas Fetzer, Speyer; Dirk Demuth, Mannheim; Heinz Rütter, Hochdorf-Assenheim; Helmuth Menig, Friedelsheim; Peter Resch, Hettenleidelheim; Wilhelm Ruppel, Frankenthal; Harro Wache, Fussgönheim, all of Germany

[73] Assignee: BASF Aktiengesellschaft, Germany

[ * ] Notice: This patent is subject to a terminal disclaimer.

[21] Appl. No.: 09/331,068

[22] PCT Filed: Dec. 9, 1997

[86] PCT No.: PCT/EP97/06855

§ 371 Date: Jun. 16, 1999

§ 102(e) Date: Jun. 16, 1999

[87] PCT Pub. No.: WO98/28250

PCT Pub. Date: Jul. 2, 1998

[30] Foreign Application Priority Data

Dec. 23, 1996 [DE] Germany ................ 196 54 046

[51] Int. Cl.$^7$ .................................................. C07C 45/29
[52] U.S. Cl. ................ 568/473; 568/383; 568/449; 568/471; 568/472
[58] Field of Search ................ 568/338, 344, 568/347, 357, 361, 383–399, 402, 449, 471, 472, 473, 489, 494, 852

[56] References Cited

U.S. PATENT DOCUMENTS

| | | | |
|---|---|---|---|
| 4,282,374 | 8/1981 | Engelbach et al. | 568/471 |
| 4,503,261 | 3/1985 | Sauer et al. | 568/471 |
| 4,555,583 | 11/1985 | Toyoda et al. | 568/473 |
| 4,814,513 | 3/1989 | Graf et al. | 568/471 |

FOREIGN PATENT DOCUMENTS

| | | |
|---|---|---|
| 7570 | 2/1980 | European Pat. Off. . |
| 271 812 | 6/1988 | European Pat. Off. . |

*Primary Examiner*—Sreeni Padmanabhan
*Attorney, Agent, or Firm*—Keil & Weinkauf

[57] ABSTRACT

The present invention relates to a process for the preparation of carbonyl compounds of the formula

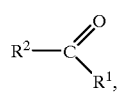

I in which $R^1$ denotes a hydrogen atom or an alkyl radical containing from 1 to 3 carbon atoms, $R^2$ denotes a hydrogen atom or a radical of the formula

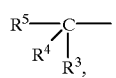

II in which $R^3$ denotes a hydrogen atom or, together with $R^4$, an oxygen atom, $R^4$ denotes the radical $OR^6$ or, together with $R^3$, an oxygen atom, $R^5$ denotes a hydrogen atom or an alkyl radical containing from 1 to 8 carbon atoms or a cyclohexyl or cyclopentyl radical, and $R^6$ denotes an alkyl radical containing from 1 to 4 carbon atoms, a cyclohexyl or cyclopentyl radical or a radical of the formula —CH$_2$—CHO or —CH$_2$—CH$_2$—O—CH$_2$—CHO, by gas-phase oxidation of methanol or alcohols of the formula

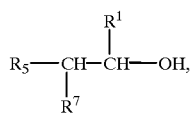

III in which $R^1$ and $R^5$ have the meanings specified above and $R^7$ denotes a hydrogen atom or a radical $OR^8$, and $R^8$ denotes a hydrogen atom, an alkyl radical containing from 1 to 4 carbon atoms, a cyclohexyl or cyclopentyl radical or a radical of the formula —CH$_2$—CH$_2$—OH or —CH$_2$—CH$_2$—O—CH$_2$—CH$_2$—OH, using an oxygen-containing gas in the presence of a (copper and/or silver)-containing catalyst and a phosphorus compound which is volatile under the conditions of the reaction and is present in an amount such that the weight of phosphorus (calculated as P), based on the weight of alcohol used, is not more than 20 ppm, wherein the amount of phosphorus used is divided into at least two portions, of which a) the first portion is added together with the mixture of gaseous starting materials before this reaches the catalyst bed and b) at least one further portion is added within the catalyst

7 Claims, No Drawings

METHOD FOR PRODUCING CARBONYL COMPOUNDS

This is the U.S. National sage Application of PCT/E897/06855 filed Dec. 9, 1997 now WO98/28250 published Jul. 2, 1998.

The invention relates to a novel process for the preparation of carbonyl compounds by gas-phase oxidation of alcohols with an oxygen-containing gas in the presence of (copper and/or silver)-containing catalysts and a phosphorus compound which is volatile under the conditions of the reaction and of which one of two portions is added to the gaseous starting mixture whilst the other portion is blended directly with the catalyst bed.

Processes for the preparation of carbonyl compounds by gas-phase oxidation over copper or silver catalysts and in the presence of a volatile phosphorus compound are known in the art.

Thus EP-A 007,570 discloses a process for the preparation of glyoxal by gas-phase oxidation of ethylene glycol with oxygen over a copper-containing oxidation catalyst in the presence of a phosphorus compound that is volatile under the conditions of the reaction, wherein the amount of phosphorus compound used is from 1 to 100 ppm based on ethylene glycol used. These processes produce unsatisfactory yields of glyoxal of not more than 70% molar, based on ethylene glycol used.

According to the processes disclosed in U.S. Pat. No. 4,282,374 and U.S. Pat. No. 4,503,261 relating to the gas-phase oxidation of ethylene glycol over copper catalysts or over a laminated catalyst comprising copper and silver crystals, advantageous results are obtained with regard to the useful life of the catalysts used and the yield of glyoxal when the reaction is carried out in the presence of a volatile phosphorus compound and the amount of phosphorus (calculated as P), based on the weight of ethylene glycol, is from 1 to 100 ppm or from 0.5 to 20 ppm respectively. However, it has been found that when these processes are operated for a lengthy period the yield of glyoxal and the purity of the product both diminish as the test period increases. This drawback is due to the increasing formation of formaldehyde and $CO/CO_2$.

In EP-B 0,271,812, it is proposed to prepare carbonyl compounds such as glyoxal by gas-phase oxidation of alcohols with an oxygen-containing gas in the presence of (copper or silver)-containing catalysts and a phosphorus compound which is volatile under the conditions of the reaction, wherein the phosphorus compound is added to the gaseous starting mixture in an amount of less than 0.5 ppm, based on the weight of alcohol used and calculated as phosphorus, before said mixture is caused to react over the catalyst. According to the process described in EP-B 0,271,812, glyoxal is obtained in yields of up to 80% molar.

The above processes of the prior art exhibit the drawback of unsatisfactory yields. In the known processes, glyoxal is obtained in the form of an aqueous solution containing glycolaldehyde, formaldehyde and organic acids as impurities. Other undesirable by-products are the resulting combustion products CO, $CO_2$ and $H_2O$. As a result of these by-products the known processes suffer from the additional drawback of unsatisfactory catalyst on-stream times.

A content of formaldehyde in the glyoxal is, in many glyoxal applications, highly undesirable on account of the toxicological properties of formaldehyde and its high reactivity. Since it is only possible to remove formaldehyde from the crude glyoxal by considerably elaborate means and at the expense of yield, for example by treatment with steam or by methods involving chemical conversion, there has been the need to find a process which makes it possible to synthesize glyoxal by the catalytic gas-phase oxidation of ethylene oxide over long on-stream periods and with substantial lack of formation of undesirable by-products.

We have now found a process for the preparation of carbonyl compounds of the formula

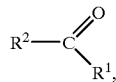

I in which $R^1$ denotes a hydrogen atom or an alkyl radical containing from 1 to 3 carbon atoms, $R^2$ denotes a hydrogen atom or a radical of the formula

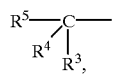

II in which $R^3$ denotes a hydrogen atom or, together with $R^4$, an oxygen atom, $R^4$ denotes the radical $OR^6$ or, together with $R^5$, an oxygen atom, $R^5$ denotes a hydrogen atom or an alkyl radical containing from 1 to 8 carbon atoms or a cyclohexyl or cyclopentyl radical, and $R^8$ denotes an alkyl radical containing from 1 to 4 carbon atoms, a cyclohexyl or cyclopentyl radical or a radical of the formula

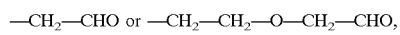

—$CH_2$—CHO or —$CH_2$—$CH_2$—O—$CH_2$—CHO, by gas-phase oxidation of methanol or alcohols of the formula

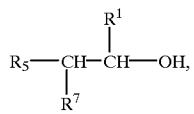

III in which $R^1$ and $R^5$ have the meanings specified above and $R^7$ denotes a hydrogen atom or a radical $OR^8$, and $R^8$ denotes a hydrogen atom, an alkyl radical containing from 1 to 4 carbon atoms, a cyclohexyl or cyclopentyl radical or a radical of the formula —$CH_2$—$CH_2$—OH or —$CH_2$—$CH_2$—O—$CH_2$—$CH_2$—OH, using an oxygen-containing gas in the presence of (copper and/or silver)-containing catalysts and a phosphorus compound which is volatile under the conditions of the reaction and is present in an amount such that the weight of phosphorus (calculated as P), based on the weight of alcohol used, is not more than 20 ppm and is preferably from 0.05 to 20 ppm, in which process the carbonyl compounds are produced in a particularly advantageous manner when the amount of phosphorus used is divided into at least two portions, of which a) the first portion is added together with the mixture of gaseous starting materials before this reaches the catalyst bed and b) at least one further portion is added within the catalyst bed, preferably in a layer representing the top 0.1 to 50% of the total depth of the catalyst bed and more preferably in a layer representing the top 1 to 35% of the total depth of the catalyst bed.

The novel process produces high yields of very pure glyoxal from ethylene glycol under conditions of continuous operation with considerably reduced formation of by-products.

In the alcohols of formula III the alkyl radicals are, for example, methyl, ethyl, propyl or butyl radicals. In the process of the invention the terminal hydroxyl groups convert to aldehyde groups and the secondary hydroxyl groups convert to keto groups.

Examples of starting compounds of formula III are the following:

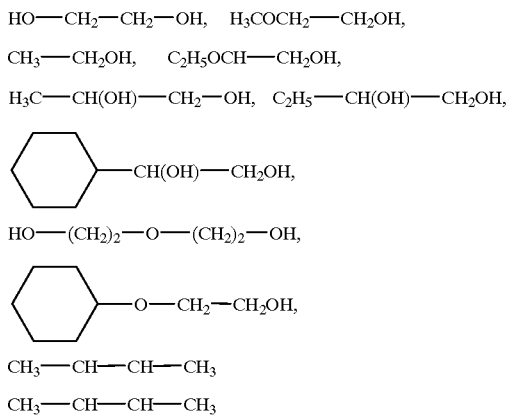

The gas-phase oxidation of the alcohol with the oxygen-containing gas over (copper and/or silver)-containing catalysts is carried out in known manner, for example at temperatures ranging from 225° to 500° C. Suitable (copper and/or silver)-containing catalysts are for example metallic copper or silver, copper-containing or silver-containing alloys or compounds with metals or non-metals, such as copper phosphides, copper bronzes or alloys of copper with silver and/or gold, copper ores such as malachite, and copper or silver compounds which can be partially or completely reduced to copper or silver during the reaction, for example copper(I) oxide, silver(I) oxide, copper(II) oxide, and compounds which convert to copper oxides on heating, such as copper nitrate and copper acetate. Also suitable are copper phosphate and copper antimonate. The copper-containing compounds may be blended with other metal oxides or non-metal oxides such as the oxides of zinc, chromium, phosphorus, antimony, tin and bismuth. The (copper and/or silver)-containing catalyst composition may be on an inert support and, if desired, diluted with an inert material. The catalyst may optionally be subjected to reductive treatment prior to use.

We prefer to use catalysts not having a large internal surface area, for example those having a surface area of less than 50 m² per gram. Of particular industrial significance are metallic copper or silver and alloys containing copper or silver as essential component. They are used, for example, in the form of turnings, wire netting, gases or alternatively as supported catalysts having, for example, an inert support or low surface area.

The phosphorus compounds volatile under the reaction conditions used are advantageously phosphorus compounds which evaporate without disintegration and do not react with the components of the synthesis gas under the conditions of the reaction. Such compounds are, for example, esters of phosphoric acid, phosphorous acid or phosphonic acid, such as trimethyl phosphate, triethyl phosphate, triisopropyl phosphate, tri-n-propyl phosphate, trimethyl phosphite, triethyl phosphite, triethylphosphine oxide, diethyl methylphosphonate, dimethyl methylphosphonate or diethyl ethylphosphonate.

The addition b) of the second or, optionally, more portions of the phosphorus used is effected, according to the present invention, within the catalyst bed, preferably in a layer representing the top 0.1 to 50% of the total depth of the catalyst bed and more preferably in a layer representing the top 0.1 to 35% of the total depth of the catalyst bed, measured down from the top of the reactor. The addition b) within the catalyst bed is preferably effected beyond the hot spot. The "hot spot" means that region of the catalyst bed at which the highest temperature occurs within the temperature profile of the catalyst bed. The temperature profile of the catalyst bed and the position of the hot spot is usually determined by measuring the temperature within the catalyst bed against the depth of the bed. This can be effected by inserting a thermosheath containing a movable thermocouple or alternatively by using a stationary multi-thermocouple having a number of points at which readings can be taken at different depths of the bed.

The addition of the amount of phosphorus used is preferably carried out in two portions preferably of from 0.05 to 10 ppm and more preferably of from 0.1 to 3 ppm, per portion.

If more than two, for example three, points of addition are used, the total amount of 20 ppm of volatile phosphorus used is preferably divided into portions of from 0.05 to 10 ppm.

The ratio, by weight, of the first portion of phosphorus used, which is added to the process upstream of the catalyst bed, to the second portion or the sum of all further portions, which is/are added to the catalyst bed, preferably downstream of the hot spot, is from 0.005:1 to 200:1, preferably from 0.033:1 to 30:1 and more preferably from 0.3;1 to 3.3:1.

The process of the invention is carried out, for example, by passing a gaseous mixture of the alcohol and water, in which the water content is from 0.1 to 99 wt %, together with air or oxygen in an amount of from 0.5 to 2.0 mol, based on 1 mol of alcohol used, and optionally together with nitrogen in an amount of up to 99 vol % of the total gas mixture, over the catalyst heated at from 225° to 500° C., the first portion of volatile phosphorus compound being added to the gaseous starting mixture whilst at least one further portion is added to the catalyst bed downstream of the hot spot in a layer representing from 1 to 35% of the total depth of the bed.

The gas mixture leaving the reactor is usually scrubbed with water.

The phosphorus compound can be added in the form of a solution in water, alcohol, preferably the alcohol used as starting material, or suitable solvents such as ethers, in liquid form or in a gaseous form achieved by evaporating the solution, or in the form of pure gaseous phosphorus compound, it being preferred to add the phosphorus in the form of an evaporated solution or in a pure gaseous form.

The glyoxal produced from ethylene glycol by the process of the invention, which may be directly obtained in commercial 40 wt % strength form, is characterized by a high degree of purity which is maintained over a long on-stream time. The process of the invention produces high yields of glyoxal over long catalyst on-stream times.

The process of the invention is described below with reference to the following examples.

EXAMPLE 1

7.2 kg of shaped copper articles were placed in a tubular reactor of stainless steel having an internal diameter of 55 mm such that the depth of the catalyst bed was 250 cm (catalyst volume 5.7 L). A synthesis gas mixture comprising 840 g/h of ethylene glycol, 1720 L(STP)/h of air and 230 L(STP)/h of nitrogen was passed through the reactor. Triethyl phosphate was added in one portion to the synthesis gas upstream of the catalyst bed and in another portion to the catalyst bed at a point from the top of the bed representing 24% of the total depth of the bed, which point was downstream of the hot spot (positioned at 15% of the total depth of the bed, measured from the top), each portion comprising 0.3 ppm of P, based on the weight of ethylene glycol used. The temperature of the reactor was maintained at 365° C. by means of a bath of fused salt.

The total gas rate comprising recirculated gas and synthesis gas was 9150-L(STP)/h.

The GHSV (gas hourly space velocity), defined as GHSV=gas volume divided by catalyst volume was 1610 $h^{-1}$.

The LHSV (liquid hourly space velocity), defined as LHSV=liquid volume divided by catalyst volume was 0.13 $h^{-1}$.

The residence time, defined as the quotient of the catalyst volume and the gas rate, was 2.3 s.

On leaving the reactor, the reaction gas was contacted by water to cause the reaction products to dissolve in the aqueous phase. The permanent gases CO and $CO_2$ remained in the exhaust gas and were analyzed in the gas phase.

Following an on-stream time of 10 days there was obtained a glyoxal yield of 81.5% molar, based on ethylene glycol used, the conversion of ethylene glycol being 99.6% molar. The combustion products CO and $CO_2$ measured 11% molar. Other by-products formed were glyoxaldehyde (0.5% molar) and formaldehyde (3.3% molar).

EXAMPLE 2

840 g/h of ethylene glycol, 1720 L(STP)/h of air and 230 L(STP)/h of nitrogen were passed through the reactor in a manner similar to that described in Example 1.

Triethyl phosphate was added in one portion to the synthesis gas upstream of the catalyst bed and in another portion to the catalyst bed at a point from the top of the bed representing 24% of the total depth of the bed, which point was downstream of the hot spot (positioned at 15% of the total depth of the bed, measured from the top), the first portion comprising 0.3 ppm of P, based on the weight of ethylene glycol used, whilst the second portion comprised 0.6 ppm of P, based on the weight of ethylene glycol used.

The GHSV, LHSV and residence time were as in Example 1. There was obtained a glyoxal yield of 80.3% molar, based on ethylene glycol used, the conversion of ethlylene glycol being 99.4% molar. There were also obtained 0.5% molar of glycolaldehyde, 2.8% molar of formaldehyde, and 12% molar of CO and $CO_2$.

EXAMPLE 3

The reaction was carried out as in Example 2, except that the air rate was 1640 L(STP)/h and the nitrogen rate 290 L(STP)/h. There was obtained a glyoxal yield of 82.8% molar, the conversion of ethylene glycol being 98.4% molar. There were also obtained 1% molar of glycolaldehyde, 1.9% molar of formaldehyde, and 9% molar of CO and $CO_2$, based in each case on the ethylene glycol used.

Comparative Example 1 (No Addition of Volatile Phosphorus Compound)

Example 1 was repeated, except that no volatile phosphorus compound was added. Purification of the product and the analysis of the gases were carried out as described in Example 1. There was obtained a glyoxal yield of 71.6% molar and the conversion of ethylene glycol was 94.3% molar. The combustion products CO and $CO_2$ were obtained in an amount of 13% molar and glycolaldehyde and formaldehyde were formed in amounts of 1.3% and 6.1% molar respectively.

Comparative Example 2 (Addition of Volatile Phosphorus Compound to the Gaseous Mixture of Starting Materials)

Example 1 was repeated except that the triethyl phosphate was added only upstream of the catalyst bed. 0.3 ppm of P, based on the weight of ethylene glycol used, was added to the synthesis gas upstream of the catalyst bed, in the form of triethyl phosphate. Purification of the product and the analysis of the gases were carried out as described in Example 1. There was obtained a glyoxal yield of 75.9% molar and the conversion of ethylene glycol was 98.9% molar. The combustion products CO and $CO_2$ were obtained in an amount of 14% molar and glycolaldehyde and formaldehyde were formed in amounts of 1.1% and 5.9% molar respectively.

Comparative Example 3 (Addition of Volatile Phosphorus Compound to the Catalyst Bed)

Example 1 was repeated except that the triethyl phosphate was added only downstream of the hot spot in the catalyst bed. 0.3 ppm of P, based on the weight of ethylene glycol used, was added to the catalyst bed at a point representing 24% of the total depth of the catalyst bed measured from the top, in the form of triethyl phosphate. Purification of the product and the analysis of the gases were carried out as described in Example 1. There was obtained a glyoxal yield of 76.9% molar and the conversion of ethylene glycol was 98.0% molar. The combustion product CO and $CO_2$ were obtained in an amount of 13% molar and glycolaldehyde and formaldehyde were formed in amounts of 1.6% and 5% molar respectively.

Table 1 below compares the yields and conversions achieved by Example 1 to 3 of the invention with those obtained in Comparative Examples C1 to C3 not covered by the invention.

TABLE 1

| Ex. | Conversion of Ethylene glycol [% molar] | Glyoxyl [% molar] | $CO/CO_2$ [% molar] | Yield of Glycol-aldehyde [% molar] | Formal-dehyde [% molar] |
|---|---|---|---|---|---|
| 1 | 99.6 | 81.5 | 11 | 0.5 | 3.3 |
| 2 | 99.4 | 80.3 | 12 | 0.5 | 2.8 |
| 3 | 98.4 | 82.8 | 9 | 1.0 | 1.9 |
| C1 | 94.3 | 71.6 | 13 | 1.3 | 6.1 |
| C2 | 98.8 | 75.9 | 14 | 1.1 | 5.9 |
| C3 | 98.0 | 76.9 | 13 | 1.6 | 5.0 |

Table 1 demonstrates the fact that the process of the invention produces higher conversions of ethylene glycol and distinctly better yields of glyoxal and a reduction in the yields of the undesirable by-products glycolaldehyde and formaldehyde.

We claim:

1. A process for the prepration of a carbonyl compound of the formula

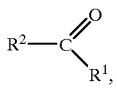

in which $R^1$ denotes a hydrogen atom or an alkyl radical containing from 1 to 3 carbon atoms, $R^2$ denotes a hydrogen atom or a radical of the formula

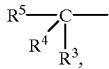

in which $R^3$ denotes a hydrogen atom or, together with $R^4$, an oxygen atom, $R^4$ denotes the radical $OR^6$ or, together with $R^3$, an oxygen atom, $R^5$ denotes a hydrogen atom or an alkyl radical containing from 1 to 8 carbon atoms or a cyclohexyl or cyclopentyl radical, and $R^6$ denotes an alkyl radical containing from 1 to 4 carbon atoms, a cyclohexyl or cyclopentyl radical or a radical of the formula

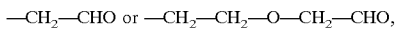

by gas-phase oxidation of methanol or an alcohol of the formula

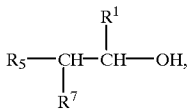

in which $R^1$ and $R^5$ have the meanings specified above and $R^7$ denotes a hydrogen atom or a radical $OR^8$, and $R^8$ denotes a hydrogen atom, an alkyl radical containing from 1 to 4 carbon atoms, a cyclohexyl or cyclopentyl radical or a radical of the formula —$CH_2$—$CH_2$—OH or —$CH_2$—$CH_2$—O—$CH_2$—$CH_2$—OH, using an oxygen-containing gas in the presence of a copper and/or silver-containing catalyst and a phosphorus compound which is volatile under the conditions of the reaction and is present in an amount such that the weight of phosphorus (calculated as P), based on the weight of alcohol used, is not more than 20 ppm, wherein the amount of phosphorus used is divided into at least two portions, of which a) the first portion is added together with the mixture of gaseous starting materials before this reaches the catalyst bed and b) at least one further portion is added within the catalyst bed.

2. A process as defined in claim 1, wherein at least one further portion b) is added to the catalyst bed within the layer representing the top 0.1 to 50% of the total depth of the catalyst bed.

3. A process as defined in claim 1, wherein at least one further portion b) is added within the layer representing the top 1 to 35% of the total depth of the catalyst bed.

4. A process as defined in claim 1, wherein the amount of phosphorus used is added in two portions.

5. A process as defined in claim 1, wherein the amount of phosphorus used (calculated as P) is from 0.05 to 20 ppm, based on the weight of alcohol used.

6. A process as defined in claim 1, wherein the ratio, by weight, of the first portion of the amount of phosphorus used to the other portion(s) is from 0.005:1 to 200:1.

7. A process as defined in claim 1, wherein glyoxal is prepared from ethylene glycol.

* * * * *

UNITED STATES PATENT AND TRADEMARK OFFICE
CERTIFICATE OF CORRECTION

PATENT NO.: 6,072,087

DATED: June 6, 2000

INVENTOR(S): FETZER et al.

It is certified that error appears in the above-identified patent and that said Letters Patent is hereby corrected as shown below:

Title page,
In the Abstract, item [57] on the front of the patent, the last line is superimposed over the beginning of the penultimate line, and the two lines should read:

--b) at least one further portion is added within the catalyst bed.--

Signed and Sealed this

Tenth Day of April, 2001

*Attest:*

NICHOLAS P. GODICI

*Attesting Officer*     *Acting Director of the United States Patent and Trademark Office*